(12) United States Patent
Dower

(10) Patent No.: US 8,382,764 B2
(45) Date of Patent: Feb. 26, 2013

(54) FEMORAL SIZING GUIDE

(75) Inventor: Liam Dower, Huddersfield (GB)

(73) Assignee: Depuy International Limited (GB)

( * ) Notice: Subject to any disclaimer, the term of this patent is extended or adjusted under 35 U.S.C. 154(b) by 1009 days.

(21) Appl. No.: 11/995,655

(22) PCT Filed: Jul. 10, 2006

(86) PCT No.: PCT/GB2006/002534
§ 371 (c)(1),
(2), (4) Date: Oct. 10, 2008

(87) PCT Pub. No.: WO2007/007067
PCT Pub. Date: Jan. 18, 2007

(65) Prior Publication Data
US 2009/0143783 A1    Jun. 4, 2009

(30) Foreign Application Priority Data
Jul. 14, 2005   (GB) .................................. 0514384.7

(51) Int. Cl.
A61B 17/60    (2006.01)
A61F 2/60    (2006.01)
(52) U.S. Cl. ........................................................ 606/88
(58) Field of Classification Search ................ 606/86 R, 606/87–89, 102
See application file for complete search history.

(56) References Cited

U.S. PATENT DOCUMENTS

| | | | |
|---|---|---|---|
| 5,486,178 A | 1/1996 | Hodge | |
| 5,624,444 A | 4/1997 | Wixon | |
| 7,115,133 B2 * | 10/2006 | Plumet et al. | 606/102 |
| 7,261,719 B1 * | 8/2007 | Twomey et al. | 606/102 |

FOREIGN PATENT DOCUMENTS

| | | |
|---|---|---|
| EP | 1470805 A1 | 10/2004 |
| FR | 2726458 A1 | 5/1996 |
| WO | WO 97/30640 | 8/1997 |
| WO | WO 03/013371 | 2/2003 |
| WO | WO 2005/046432 | 5/2005 |
| WO | WO 2005/055838 | 6/2005 |

OTHER PUBLICATIONS

PCT Written Opinion, 6 pages.
International Search Report, dated Jun. 19, 2007, 4 pages.
UK Search Report, dated Oct. 26, 2005, 3 pages.
International Preliminary Report, Nov. 9, 2007, 11 pages.

* cited by examiner

*Primary Examiner* — Anu Ramana

(57) ABSTRACT

An instrument for use in determining an anterior-posterior dimension of a femur during a minimally invasive surgical procedure includes a body having a base and a member extending upwardly from the base, said member providing a first part of a sliding mechanism. A stylus includes a stylus support providing a second part of a sliding mechanism which can engage with the member to allow relative sliding movement between the stylus and base, and a stylus member mounted on the stylus support. An implant size indicator interacts with the sliding mechanism to be moved relative to a scale by the member to indicate a size of an implant corresponding to the relative positions of the body and stylus.

18 Claims, 7 Drawing Sheets

FEMORAL SIZING GUIDE

The present invention relates to an instrument and to methods for use in knee arthroplasty. In particular the present invention relates to an instrument and to methods for use in determining the anterior-posterior dimension of a femur during knee arthroplasty.

Known techniques for determining the anterior-posterior dimension of a distal part of a femur generally involve the use of a template or sizing guide. Such methods generally involve measuring the anterior-posterior dimension of the distal part of the femur with the knee joint in about 90° flexion. For example, US-2003/0171757 describes a method and instrumentation for determining the anterior-posterior dimension of a distal femur. The anterior-posterior size guide described in US-2003/0171757 includes a base having a first end and a second end and a support extending upwardly from the first end of the base. The support provides a first elongated slot extending throughout a major portion of the support. The first elongated slot extends substantially parallel to the base and in a direction from the first end of the base towards the second end of the base. The support also provides a second elongated slot which is in communication with and extends orthogonal to the first elongated slot.

Scale markings are provided adjacent to the first elongated slot on the outer surface of the support. A plunger rod having a first end and a second end extends through an aperture provided in the upper end of the support into the first elongated slot of the support. A slidable member providing an alignment hole is positioned within the first elongated slot of the support and is connected to a first end of the plunger rod. A stylus having a femoral engagement surface which extends substantially parallel to the base of the size guide is positioned between the second end of the plunger rod and the upper end of the support. The stylus and the slidable member are movable towards and away from the base. As the stylus and slidable member are moved towards and away from the base the alignment hole of the slidable member moves along the scale markings on the surface of the support.

In use, the anterior-posterior size guide is positioned with the base contacting the posterior femoral condyles when the knee is in flexion. The stylus and the slidable member are moved towards the base until the femoral engagement surface of the stylus contacts the resected surface of the distal end of the femur. The plunger rod is then secured in place. The position of the alignment hole of the slidable member along the scale on the support determines the anterior-posterior dimension of the distal end of the femur.

While these known techniques are generally adequate for use during open knee surgery, they are not always appropriate for use in minimally invasive procedures. During minimally invasive procedures a small incision is made in the knee joint. The prior art methods require the knee to be placed in about 90° flexion. When the knee joint is placed in flexion the skin surrounding the small incision in the knee joint tightens as the skin moves distally away from the joint. As the skin surrounding the incision tightens it becomes increasingly difficult to insert the prior art assemblies into the knee joint. The size of the prior art assemblies therefore imposes a minimum limit on the size of the incision which can be made in the knee joint. There are indications that the larger the incision made in the knee joint the longer the recovery time of the patient.

Traditionally, surgeons have attempted to address this problem by performing an additional surgical step of removing an initial section of the anterior cortex prior to determining the anterior-posterior dimension of the femur to provide additional space within the joint. Carrying out an additional surgical step is disadvantageous. The additional surgical step involves the use of further instrumentation to make the initial cut. Furthermore, the making of the initial cut can have an influence on the final positioning of the implant.

It has been found that as the knee joint is flexed the small incision in the knee moves distally away from the distal femur. The window provided by the incision therefore moves distally away from the knee joint and it can be difficult for the surgeon to assess whether the stylus is in contact with the anterior cortex of the distal femur. This increased difficulty in visually assessing the positioning of the stylus can lead to errors in determining the anterior-posterior dimension of the femur.

According to a first aspect of the invention, there is provided at least one instrument, or a kit of parts or instruments, for use in determining an anterior-posterior dimension of a distal femur during minimally invasive surgery selected from the following: a size guide body having a base and a member extending upwardly from the base; a stylus including a support and a stylus member; an implant size indicator is slidably moveable by interaction with the stylus or size guide body; a drill guide; and an anterior cutting block.

A further aspect of the invention provides a kit of parts for use in determining an anterior-posterior dimension of a femur during a surgical procedure. The kit of parts can include a body comprising a base, and a member extending upwardly from the base and providing a first part of a sliding mechanism. The kit can also include a stylus comprising a stylus support and a stylus member. The stylus support can provide a second part of the sliding mechanism which can engage with the member to allow relative sliding movement between the stylus and base. The kit can further comprise an implant size indicator which can interact with the sliding mechanism to indicate a size of an implant. The indicator can be moved relative to a scale by relative sliding of the stylus and body. The indicator can indicate a size of an implant corresponding to the relative positions of the body and stylus.

Preferably, the indicator is moved by interaction of the indicator with a part of the stylus, a part of the body or a part of the member.

Various features of the individual instruments or parts, and combinations of the various instruments, allow a minimally invasive knee arthroplasty to be carried out so that the femur can be accurately resected and damage to surrounding muscles, tendons, ligaments and soft tissue is reduced. The recovery of a patient is also potentially reduced and the accuracy of the procedure is improved.

The kit, and instruments of the present invention have various advantages. Preferably, the femoral size guide comprises at least two discrete components, the size guide body and a stylus. The components of the femoral size guide can therefore be inserted separately through an incision into the knee joint. The femoral size guide can be assembled within the joint once the components have been inserted separately and positioned within the knee joint. The present invention therefore has the advantage that the minimum size of an incision in the knee is reduced compared to prior art devices as the femoral size guide of the present invention can be inserted into the joint as separate components. As the size of the incision required for insertion of the femoral size guide of the present invention is reduced compared to the size of the incision required for prior art assemblies the recovery of a patient is also potentially reduced.

For example, at least the size guide body and the stylus are discrete components which can be engaged to provide a femoral sizing guide.

Preferably the size guide body and stylus can be engaged and wholly separated.

The size guide body and stylus can between them provide a sliding mechanism allowing the body and stylus to be slid relative to each other. The sliding mechanism can interact with the implant size indicator to cause the implant size indicator to slide relative to the stylus or body so as to indicate the size of the implant.

The sliding mechanism can be provided by a male component and a female component. The male or female component can be provided by a part of the stylus and a part of the body can provide the other component. Preferably, the stylus provides the male component and the body provides the female component.

The size guide body can include a tubular member. The tubular member can extend substantially orthogonal to the base of the sizing guide body. The tubular member of the size guide body can have a first end which is attached to the base and a second end which includes an aperture of a channel extending at least partially along the longitudinal axis of the member. The channel can extend longitudinally from the aperture provided by the second end of the tubular member towards the base.

The stylus can include a stylus member and a stylus support. The stylus support can be in the form of an elongate shaft. The elongate shaft can comprise a first end and a second end. Preferably, at least part of the first end of the elongate shaft can be removably received within the channel provided by the tubular member of the size guide body.

Preferably, the stylus includes a scale provided by markings which indicates the sizes of an implant. The scale can be provided on the shaft and can be provided on the surface of at least a portion of the elongated shaft. Preferably, the scale extends longitudinally from the first end of the elongated shaft towards the second end of the elongated shaft.

Preferably, the cross-sectional or lateral dimension of the second end of the elongated shaft can be greater than the cross-sectional dimension of the channel of the tubular member of the size guide body.

Preferably, the implant size indicator is slidably moveable along the shaft of the stylus. The indicator can be slidable between the second end of the elongated shaft and the first end of the shaft, or second end of the tubular member. The indicator can be in the form of a collar. The collar can have a cross-sectional dimension which is greater than the cross-sectional dimension of the channel in the tubular member. Preferably, in use the position of the collar along the elongated shaft of the stylus indicates the anterior-posterior dimension of the distal femur.

Preferably, the implant size indicator includes a locking member for securing the indicator in position. The indicator can slide on a shaft part of a telescoping shaft and socket (or channel) arrangement. For example, the indicator can be a collar on the shaft. The collar can be a friction fit on the shaft, so that frictional forces tend to hold the collar in a particular location on the shaft unless it is forcibly moved. The collar can be locked on the shaft by means of a threaded locking screw. The collar can incorporate a spring which acts between the collar and the shaft and gives rise to frictional forces which tend to hold the collar in a particular location on the shaft unless it is forcibly moved. The spring might for example force a detent to engage one of a series of notches or other recesses which are spaced apart along the shaft (in the manner of a rack).

Preferably, the second end of the stylus support provides a further channel. Preferably, the further channel extends substantially perpendicular to the longitudinal axis of the elongated shaft. Preferably, a part of the stylus member extends through the further channel provided by the stylus support. Preferably, the stylus member can be translated relative to the is stylus support, for example by sliding within the further channel. Preferably the stylus member can also pivot relative to the body part. Preferably, the cross-sectional dimensions of the second end of the elongated shaft are greater than the cross-sectional dimensions of the first end of the elongated shaft.

Preferably, the femoral sizing guide comprises at least three discrete components. For example the size guide body, the stylus (comprising the stylus support and stylus member as an integral unit) and the implant size indicator, or collar, are three discrete components of the femoral size guide. Preferably, the femoral size guide comprises at least four discrete components. For example the size guide body, the elongated stem of the stylus, the arm of the stylus and the collar are four discrete components of the femoral sizing guide. For example the size guide body, the stylus, the collar and the locking member are four discrete components of the femoral size guide.

Preferably, the base of the size guide body has a first end and a second end which are connected by a central portion. Preferably, the tubular member extends upwardly from the central portion of the base. Preferably, the first end of the base provides a first foot and the second end of the base provides a second foot which cooperate with the central portion to define a U-shaped base. Preferably the first and second feet of the base are contacted with the posterior femoral condyles of the joint.

Preferably, the tubular member of the base provides a scale including markings corresponding to the dimensions or sizes of implants.

Preferably, the surface of the size guide body which contacts the distal femur additionally comprises at least one spike, preferably at least two spikes, for example four spikes.

Preferably, the surface of the size guide body which contacts the distal femur provides at least one aperture, preferably at least two apertures, for example four apertures. The size guide body is attached to the distal femur by at least one screw or pin which is inserted through the at least one aperture provided by the surface of the size guide body which contacts the distal femur.

Preferably, the elongated shaft of the stylus support is rotatable about the longitudinal axis of the elongated shaft within the tubular member of the size guide body.

Preferably, the arm comprises a first portion and a second portion. Preferably, the first portion of the arm has a first end and a second end. Preferably, the first portion of the arm extends through the further channel. Preferably, the first portion of the arm is slidably received within the channel provided by the second end of the elongated shaft. Preferably, the first portion of the arm extends substantially parallel to the base. Preferably, the second portion of the arm is connected to and extends at an angle from the first end of the first portion of the arm towards the base of the size guide body. Preferably, the second portion of the arm provides an arc which extends from the first end of the first portion of the arm towards the base of the size guide body. Preferably the stylus member terminates in a stylus tip.

Preferably, a scale of markings are provided along the upper surface of the first portion of the arm. Preferably, the scale of markings corresponds to different sizes of implant required. Preferably, the size of implant required is determined from reading the scale marking on the first portion of the arm which is adjacent to an opening of the channel at the second end of the elongated shaft.

Preferably, the femoral size guide additionally comprises a handle which is attached to the arm. Preferably the femoral size guide additionally comprises a handle which is attached to the second end of the first portion of the arm of the stylus. Preferably, the handle enables the surgeon to slide the first portion of the arm within the channel in the second end of the elongated shaft. Preferably, the handle enables the surgeon to rotate the arm and the elongated shaft of the stylus about the longitudinal axis of the elongated shaft within the tubular member of the size guide body. Preferably, rotation of the arm of the stylus enables the surgeon to assess the femoral surface.

Preferably the elongated shaft of the stylus has any suitable cross-section for enabling the elongated shaft to be rotated within the tubular member of the size guide body about the longitudinal axis of the tubular member. For example, the elongated shaft of the stylus has a circular cross-section.

Preferably, the channel provided by the second end of the elongated shaft and the arm of the stylus have suitable cross-sections which prevent rotation of the arm about the longitudinal axis of the channel. For example, preferably the arm of the stylus and the channel have rectangular cross-sections.

The implant size indicator can have any suitable cross-sectional shape and dimensions in order to interact slidingly with the sliding mechanism provided by the stylus and body. The implant size indicator can be a collar. For example, the collar can have a circular, hexagonal, octagonal, triangular or square cross-section. Preferably, the collar has a circular cross section. More preferably the collar is an O-ring.

Preferably, the collar includes a locking member. The locking member may be any suitable means known in the art for securing the collar to the elongated shaft. Preferably, the locking member comprises a spring-loaded lock. Preferably, the spring-loaded lock is actuated by friction or by a screw.

Preferably the collar is composed of a metal, such as stainless steel or a polymeric material such as rubber.

Preferably, at least one of the stylus and the femur sizer body is composed of stainless steel. Preferably, the stylus and the femur sizer body are composed of stainless steel.

Preferably, the kit of the present invention also includes at least one instrument or part selected from: a drilling guide; and an anterior cutting block.

Preferably, the kit of the present invention includes a cutting guide. Preferably, the cutting guide can be slidingly engaged with the body and can be capable of referencing an anterior cut. The kit of the present invention therefore has the advantage that a drill guide is not required and therefore the kit comprises a reduced number of components.

According to a further aspect of the invention, there is provided an assembly comprising any combination of any of the parts of the kit aspect of the invention mentioned above.

According to a further aspect of the invention, there is provided a method for determining the anterior-posterior dimension of a distal femur during a minimally invasive surgical procedure using a femoral size guide. The method can comprise inserting a body of the femoral size guide between a distal femur and a proximal tibia while the knee is in flexion. A base part of the body can be put in contact with the posterior condyles of the distal femur. A part of a stylus can be slidingly engaged with a part of the body. The stylus can be slid relative to the body of the size guide with the knee in extension until a stylus member of the stylus contacts a portion of the distal femur. The anterior-posterior size of the distal femur can be determined from the position of an implant size indicator which has been caused to by the relative sliding movement of the stylus and body.

The stylus part can be wholly or partially removed from the body part prior to determining the anterior-posterior size.

According to a further aspect of the invention, there is provided a method for determining the anterior-posterior dimension of a distal femur during minimally invasive surgery. The method can comprise some or all of the following: placing the knee joint in flexion and making an incision in the knee; resecting the distal femur; resecting the proximal tibia; whilst the knee joint is in flexion inserting the size guide body of the femoral size guide onto the distal femur so that the base of the size guide body contacts the posterior condyles of the distal femur; placing the knee joint in extension so that the tubular member of the size guide body is present between the proximal tibia and distal femur and inserting the elongated shaft of the stylus of the femoral size guide into the channel provided by the tubular member; whilst the knee joint is in extension slidably moving the elongated shaft of the stylus towards the base until the arm portion is contacted by a portion of the anterior aspect of the distal femur; whilst the knee joint is in extension slidably moving the collar along the elongated shaft of the stylus until the collar contacts the second end of the tubular member of the base and securing the collar in position along the elongated shaft; and removing the elongated shaft of the stylus from the channel provided by the tubular member of the size guide body; and determining the anterior-posterior dimension of the distal femur from the position of the collar along the elongated shaft and the markings along the elongated shaft of the stylus.

Preferably, the method further includes the step of slidably moving the arm of the stylus within the channel provided in the second end of the elongated shaft. Preferably, the method further includes the step of assessing the position of the exit point of the anterior femoral cut relative to the size of the implant selected from the scale markings on the arm by rotating the stylus about the longitudinal axis of the elongated shaft of the stylus.

Preferably, the method further includes the step of determining the size of the implant required from the scale markings on the arm adjacent to an opening of the channel provided by the second end of the elongated shaft of the stylus.

As the method uses the instruments to measure the anterior-posterior dimension of the femur when the femur is in extension the skin around the incision is not stretched or tightened. Furthermore, the window provided by the incision is moved proximal to the knee joint and the surgeon is provided with an improved view of the knee joint. The surgeon is therefore able to more accurately assess whether the instrument of the present invention have been accurately positioned in the knee joint. The incision in the knee is smaller using the method of the present invention than for conventional methods as the skin around the incision is not tightened.

Resection of the tibia can occur when the knee is in extension or flexion. Resection of the tibia may involve making a conservative cut in order to provide sufficient space for the size guide body within the joint.

Preferably, the method comprises the further step of rotating the stylus within the channel provided by the tubular member so that the arm of the stylus correctly locates the femur.

Preferably, the size guide body is inserted through the incision and placed between the femur and the tibia whilst the knee is in flexion, preferably when the knee is in about 90° flexion. Preferably the base of the size guide body contacts the distal femur. Preferably, the first foot and second foot of the base contact the posterior femoral condyles when the knee is in flexion. Preferably, the surface of the base of the size guide body which contacts with the distal femur comprises at least one spike for securing the base to the distal femur.

Preferably, the first foot and second foot of the base of the size guide body comprise at least one spike for securing the base to the posterior condyles of the femur. Preferably the base of the size guide body comprises at least two spikes, more preferably at least three spikes, for example five spikes.

Preferably, the base of the size guide body provides at least one opening. Preferably, at least one screw or pin is inserted through the opening provided the base of the size guide body and attaches the size guide body to the distal femur.

Preferably, after the size guide body has been inserted the knee joint is then extended.

Preferably, the knee joint is fully extended. Preferably, the base of the size guide body which is in contact with the distal femur, preferably in contact with the posterior condyles of the femur, is shaped so that when the knee joint is moved from a position wherein the knee is in flexion to a position wherein the knee is extended the size guide body is able to move with the distal femur without making contact with the proximal tibia.

Preferably, the base of the size guide body is sufficiently thin so that the base does not make contact with the proximal tibia when the knee joint is moved from a flexed position to an extended position. The initial surgical steps in resecting a distal femur involve performing the distal femoral cut and the proximal tibial cut. Generally, these cuts provide a gap, when the knee joint is in extension of less than about 20 mm, for example about 17 mm.

Preferably, the base of the size guide body has a thickness, i.e. the dimension of the base between the surface of the base adjacent to the tibia and the surface of the base which is in contact with the femur, of less than about 20 mm, more preferably less than about 18 mm, for example less than about 17 mm. Preferably, the base portion has a thickness of more than about 10 mm, more preferably more than about 12 mm, for example about 15 mm.

The tubular member may have any suitable cross-sectional shape, for example the tubular member can have a circular, hexagonal, octagonal, triangular or square cross-section.

Preferably, the tubular member has a cross-sectional dimension of less than about 19 mm, more preferably less than about 18 mm, for example less than about 17 mm. Preferably, the tubular member has a cross-sectional dimension of more than about 10 mm, more preferably more than about 12 mm, for example about 15 mm.

When the knee joint is extended the tubular member of the size guide body is preferably located between the proximal tibia and the distal femur. Preferably, the tubular member of the size guide body is substantially parallel to the anterior-posterior axis of the distal femur. When the knee joint is extended the incision moves proximally and therefore enables the surgeon to have improved visual access to the anterior cortex. Preferably, the tubular member can be visibly located through the incision. The present invention therefore has the advantage that the surgeon is able to visibly locate the tubular member of the size guide body within the knee joint when the knee is in extension.

The visible end of the tubular member is used as a reference point for determining the size and shape of the stylus shaft. Preferably, the surgeon selects a stylus having an elongated shaft having the appropriate cross-sectional shape and dimensions for being received within the channel of the tubular member of the size guide body.

Preferably, the elongated shaft of the stylus is inserted within and moved towards the base of the sizer body guide until the arm of the stylus contacts the distal femur. Preferably, the collar is moved along the elongated shaft from the second end of the shaft until the collar contacts the first end of the tubular member. Preferably the collar is secured in position against the elongated shaft of the stylus. Preferably the collar is composed of a material which is able to secure the collar against the elongated shaft. Preferably the collar is composed of an elastomeric material and the collar is placed in tension when placed around the elongated shaft of the stylus. The tension present within the collar secures the collar in position about the elongated shaft of the stylus. Preferably the collar is composed of a metal, for example steel. Preferably the collar is locked in position by a locking member. Preferably, the locking member comprises a spring-loaded lock. The locked position of the collar on the elongated shaft aligns with markings which extend longitudinally along at least a portion of the elongated shaft. Each marking corresponds to the anterior-posterior dimension of the distal femur. The anterior-posterior dimension of the distal femur can therefore be determined from the location of the collar along the markings provided on the elongated shaft. Therefore the size of implant required can be determined from the position of the collar on the elongated shaft. Preferably, the stylus is removed from within the channel of the tubular member and the position of the collar is determined.

Preferably, the arm is slidably moveable within a channel provided in the second end of the stylus. Preferably, the surgeon adjusts the length of the arm accordingly so that the arm is adjusted to a position corresponding to the size of implant required as indicated by the position of the collar on the elongated shaft of the stylus. Preferably, the surgeon re-inserts the elongated shaft of the stylus with the collar locked in position within the channel of the size guide body and rotates the stylus so that the arm contacts the femur. Rotation of the stylus will enable the surgeon to assess the position of the exit point of the anterior femoral cut relative to the size of the implant as determined by the scale markings on the arm. The surgeon may carry out an iterative process of adjusting the length of the arm of the stylus to correspond to a different sized implant which may then change the position of the collar along the elongated shaft of the stylus. Once the surgeon is satisfied with the readings from the scales on the elongated shaft and the arm of the stylus the surgeon can select the appropriate size of implant for the femur. The method of the present invention therefore has the advantage that the correct size implant for each patient can be determined with reduced risk of further injury to the patient.

The stylus is then removed from the size guide body. The knee is placed in flexion. Preferably, a drill guide is inserted onto the tubular member of the size guide body. Preferably, the drill guide comprises a channel which receives the tubular member of the size guide body. The drill guide is adjusted to the appropriate height as indicated by the scale on the tubular member of the size guide body for the selected size of the desired implant. The drill guide is secured in place and reference holes are drilled into the femur. The drill guide and the size guide body are then removed from the joint. An anterior cutting block is then attached to the reference holes in the femur and the anterior femoral cut is made.

After the stylus has been removed from the size guide body an anterior cutting block can be inserted onto the tubular member of the size guide body and the anterior femoral cut is made. This method therefore has the advantage that a separate drill guide is not required.

Once the femur has been resected, the femoral implant is inserted and the surgical site is closed.

An embodiment of the present invention will now be described, by way of example only, and with reference to the accompanying drawings, in which.

Like items shown in the Figures share common reference signs unless indicated otherwise.

Figure 1:
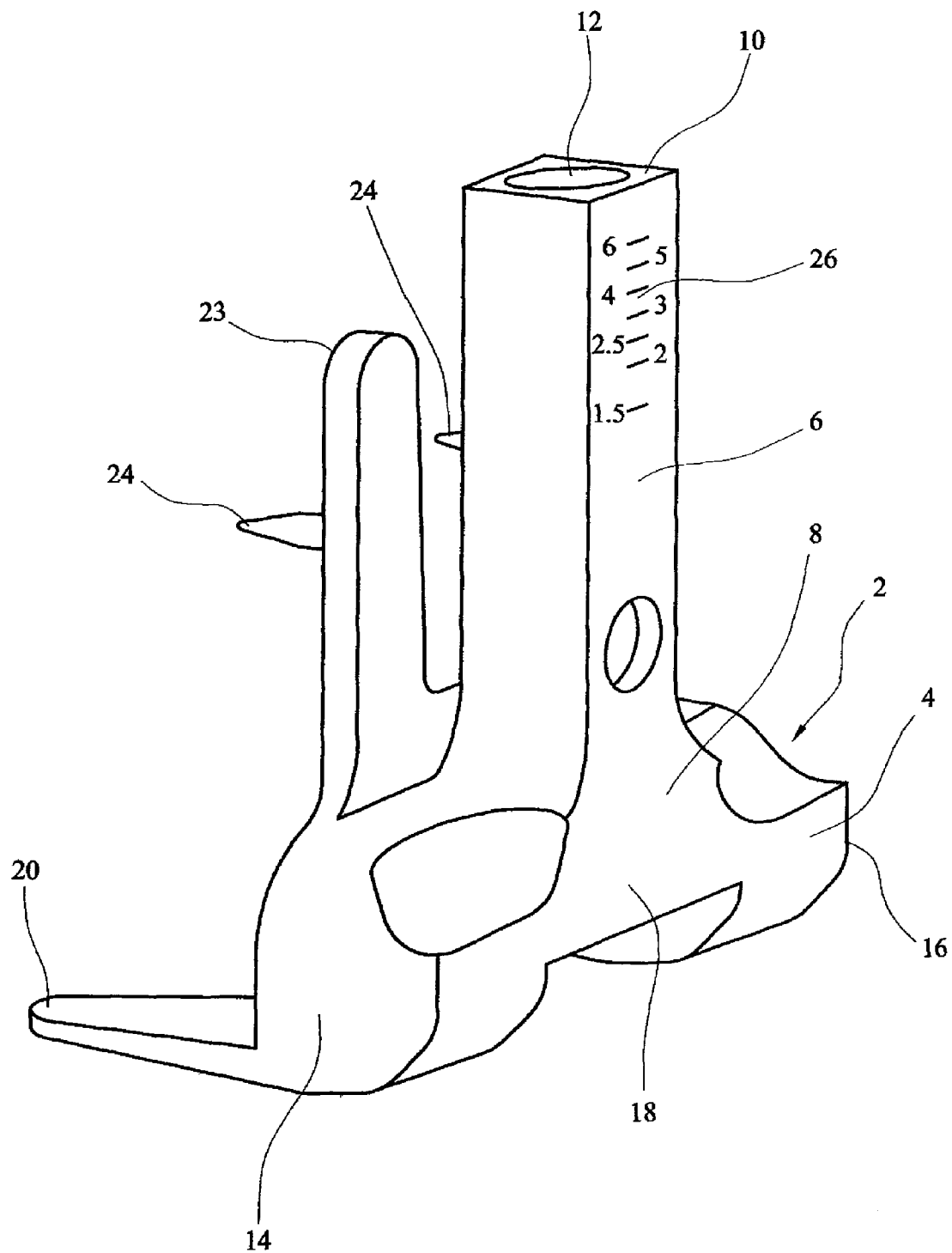
FIG. 1 illustrates a perspective view of a size guide body part of the present invention.

With reference to FIG. 1, the size guide body 2 comprises a base 4 and a member 6 extending upwardly from the base 4 in the form of a square tube. The member 6 extends substantially orthogonally from the plane of base 4. The member 6 has a first end 8 which is attached to the base 4 and a second end 10 including an aperture or opening 12 to a circular cross section channel or bore. The channel extends longitudinally along the member 6 from the aperture 12 at the second end 10 of the member 6 towards the first end 8 of the tubular member 6. The member provides a first female part of a sliding mechanism.

The base 4 has a first end 14 and an opposed second end 16 which are connected by a central portion 18. The first end 14 of the base 4 provides a first foot 20 and the second end 16 of the base 4 provides a second foot 22 which cooperate with the central portion 18 to provide a U-shaped portion of the base with member 6 extending from the central portion 18 of the base 4. The base 4 also includes first 23 and second 23' limbs each bearing a respective spike 24 which extends from an inner surface of the limbs 23, 23'. The spikes can contact the distal femur in use as will be described in greater detail below. The member 6 also has a scale of markings 26 corresponding to the dimensions or sizes of implants.

The thickness of the base between those parts that engage the resected surface of the femur in use and the opposing resected surface of the tibia is less than about 20 mm to allow the base to fit within the space available in the minimally invasive approach provided by the present invention. For example, the thickness of the thickest part of the base, eg central portion 8 can be about 17 or 18 mm or less if possible. Also the base has a shape allowing the knee to be flexed and extended with the body in situ attached to the distal femur without contacting the proximal tibia. For example, the base includes cut out portions and chamfered edges toward the proximal edge of the base.

Figure 2:
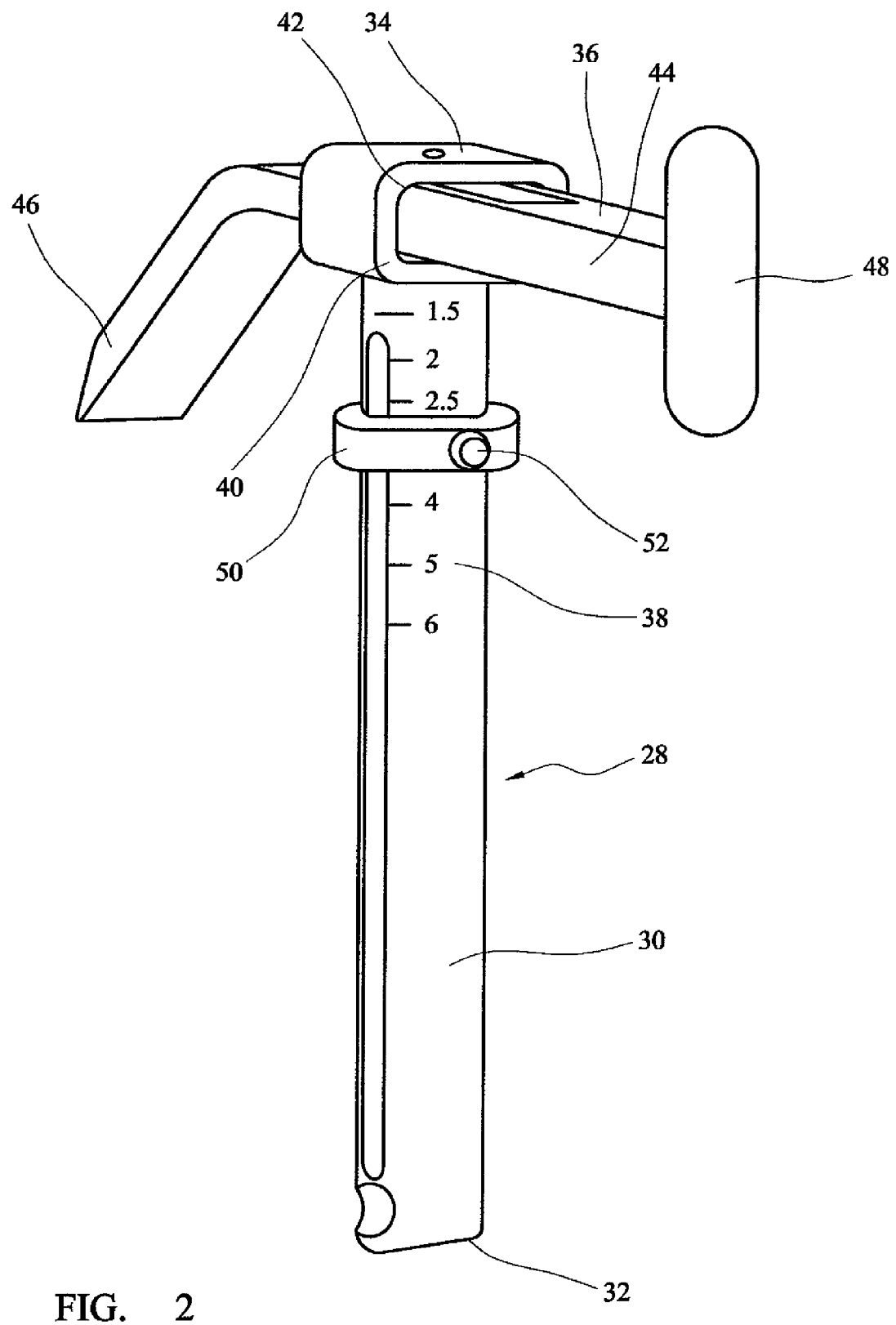
FIG. 2 illustrates a perspective view of a stylus part of the present invention.

FIG. 2 shows a stylus part 28 comprises a stylus support in the form of an elongated shaft 30 having a first end 32 and a second end 34 and a stylus member in the form of an arm 36. The elongate shaft 30 provides a male part of a sliding mechanism. The elongated shaft 30 includes a scale of markings 38 extending from the second end 34 of the elongated shaft 30 towards the first end 32 of the elongated shaft 30. The shaft 30 is partially hollow having an aperture extending along the majority of the longitudinal axis of the shaft. The shaft has a generally curved cross section with a size substantially matching that of the channel in the member 6, such that the shaft can be received in the channel and can slide along the longitudinal axis of the channel thereby providing a sliding mechanism by which body and stylus can slid relatively. The stylus can also rotate about shaft 30 in the channel. In other embodiments, the stylus support can include a channel providing a female part and the base member 6 can provide a male part received therein to provide an alternative sliding mechanism.

The second end 34 of the elongated shaft 30 includes a formation defining a further channel 42 which extends perpendicularly to the longitudinal axis of the elongated shaft 30. The stylus member arm 36 comprises a first portion 44 and a second portion 46. The first portion 44 of the arm 36 is slidably received within channel 42 at the top of the stylus support. The first portion 44 of the arm 36 and the channel 42 have rectangular cross-sections in order to prevent rotation of the arm 36 within the channel 42. The first portion also includes a channel therein which can co-operate with a pin extending across channel 42 to guide and retain arm 36 within channel 42. The cross-sectional or lateral dimensions of the formation at the second end 34 of the elongated shaft 30 are greater than the cross-sectional dimensions of the first end 32 of the elongated shaft 30. The second portion 46 of the arm 36 extends from the first portion 44 of the arm 36 and extends downwardly at an angle therefrom and terminates in a tip. A handle 48 provided at the other end of the arm 36. The first portion 44 of the arm 36 also includes a scale of markings (not shown) which indicate the corresponding size of implant to be used.

An implant size indicator in the form of collar 50 is mounted about shaft 30 and is slidable from the first end 32 of the elongated shaft 30 toward the second end 34 of the elongated shaft 30. The collar 50 further comprises a locking member 52 for securing the collar 50 in position on the elongated shaft 30. The locking member 52 can be a grub screw or similar.

Figure 3:
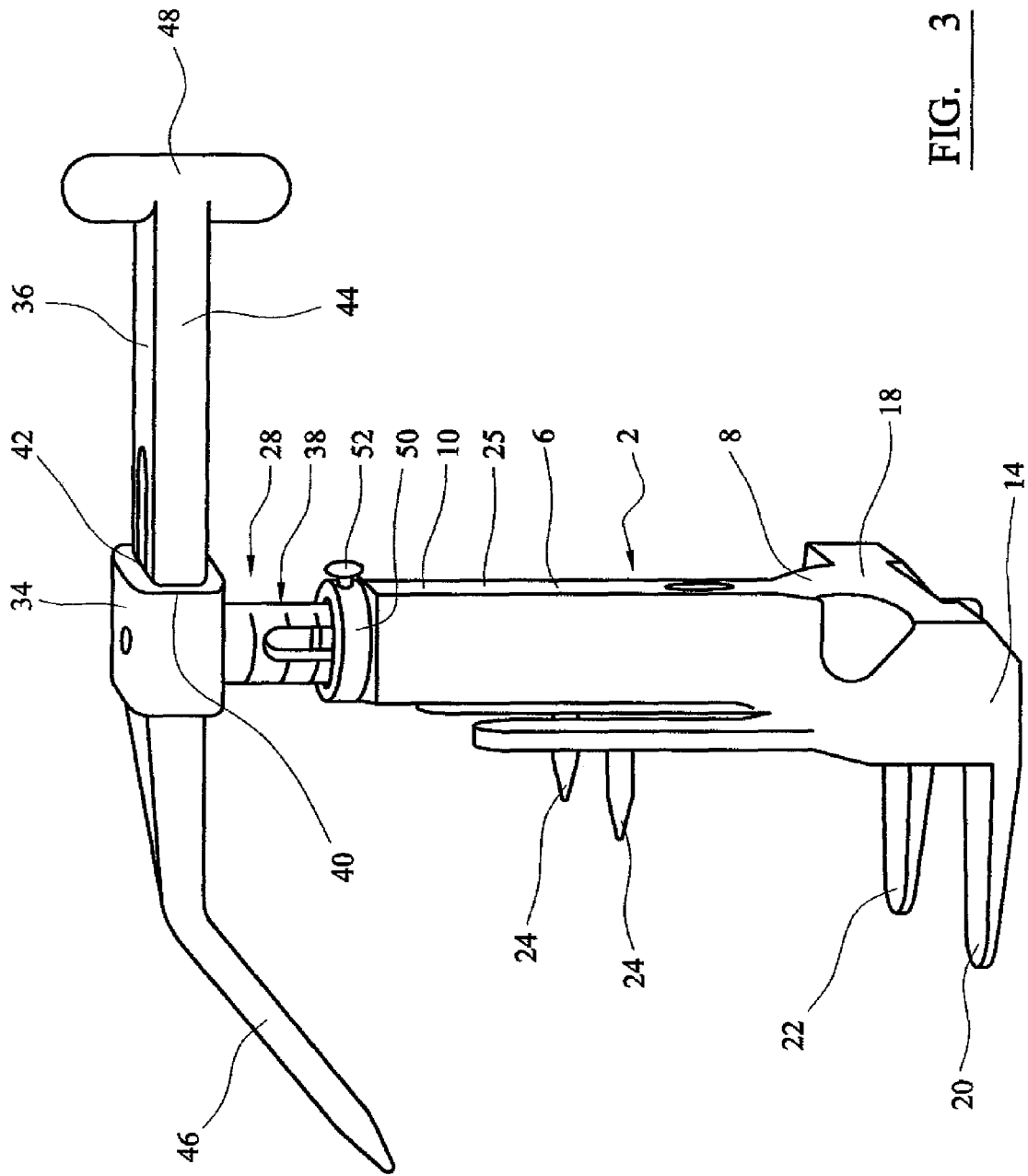
FIG. 3 shows a side view of a femoral size guide of the present invention.
Figure 4:
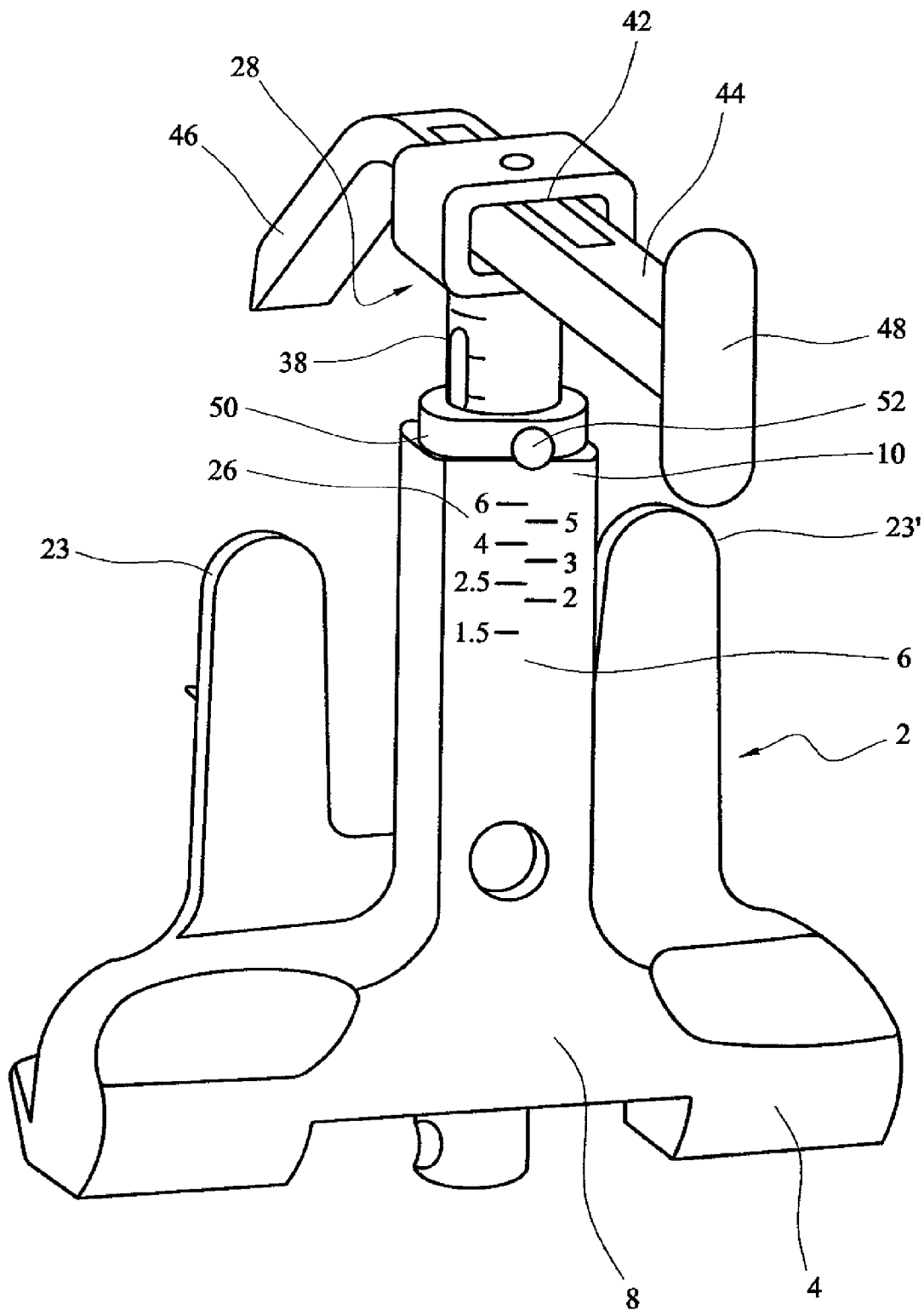
FIG. 4 shows a front view of the femoral size guide shown in FIG. 3.

With reference to FIGS. 3 and 4, there is shown an assembly of the base and stylus parts. The first end 32 of the elongated shaft 30 of the stylus 28 is slidably received within the channel provided by the tubular member 6 of the size guide body 2.

Figure 5:
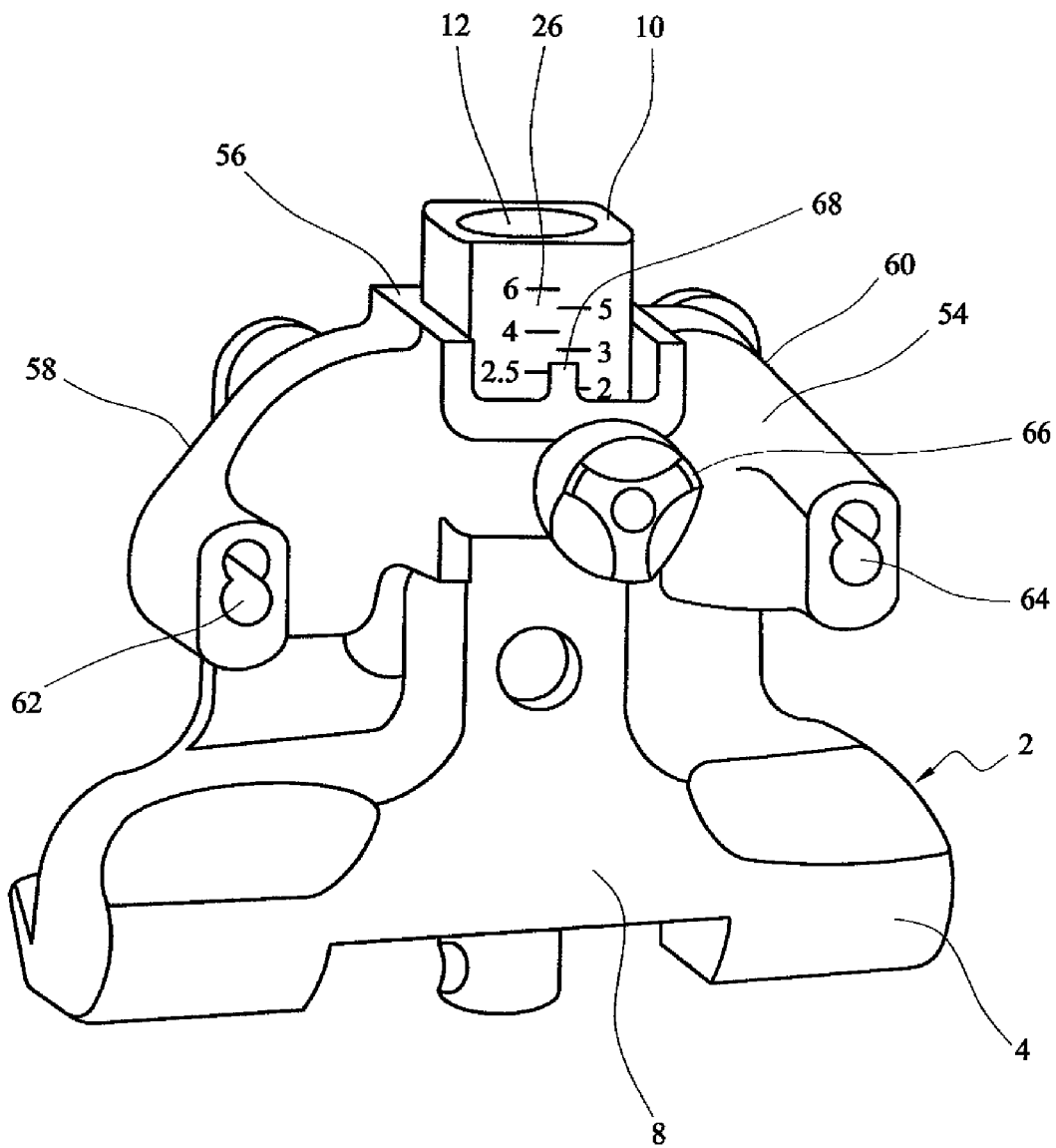
FIG. 5 shows a front view of the size guide body and a drill guide part of the present invention.

With reference to FIG. 5 there is shown a drill guide part 54 slidably received on the tubular member 6 of the size guide body 2. Drill guide 54 includes a central portion 56 with a channel there though sized to fit snugly about member 6. First and second arms 58, 60 extend from opposing sides of the central portion and include respective apertures 62, 64 therein for receiving a fixing in use. Each aperture 62, 64 is in the form of two partially overlapping circular holes, such that each aperture has a generally figure of eight shape. Central portion 56 also includes a formation with a threaded bore therein for receiving a threaded fixing 66. Central portion 56 also bears a pointer 68 which in use co-operates with scale 26.

Figure 6:
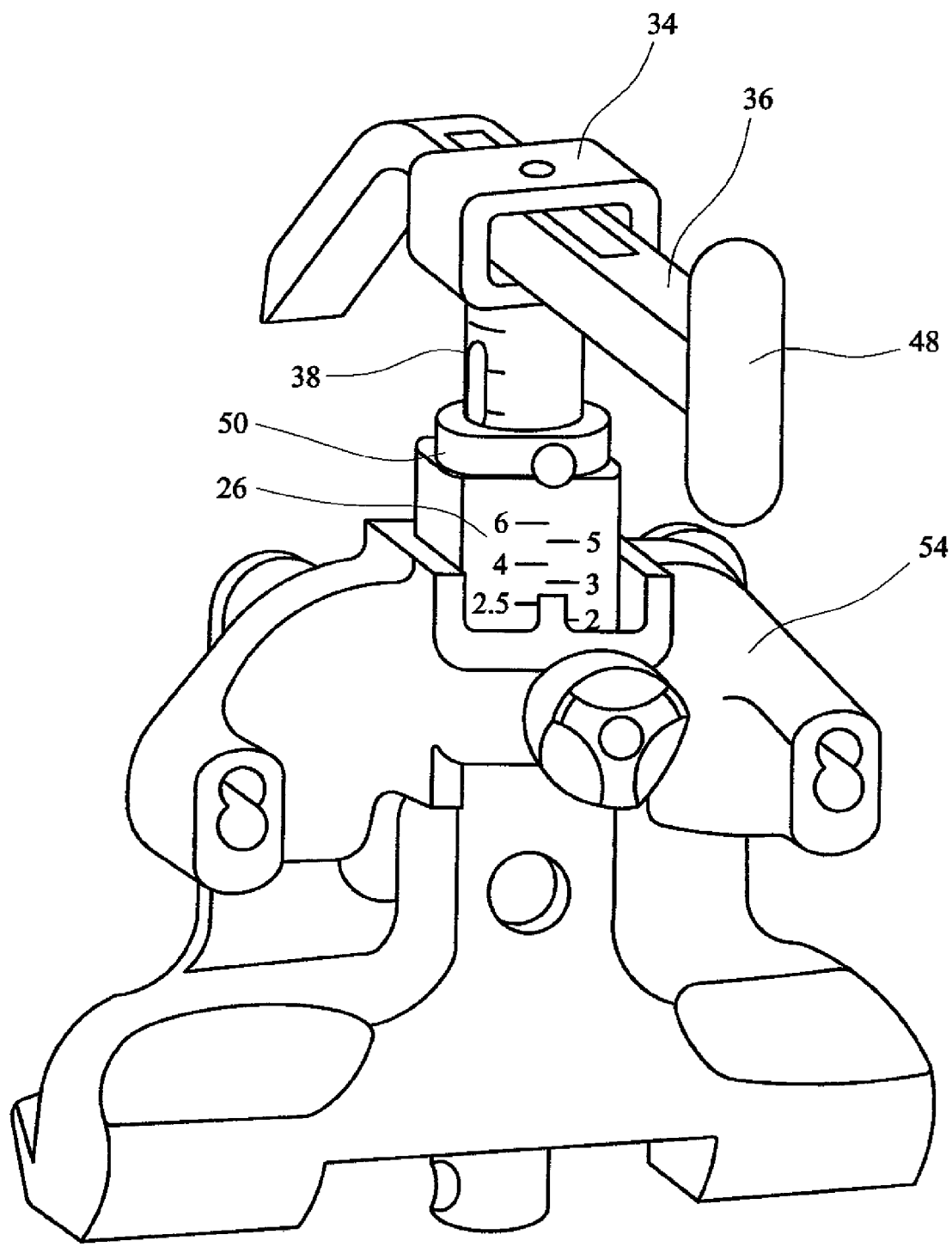
FIG. 6 shows a front view of the femoral size guide including the drill guide part according to the present invention.

FIG. 6 shows an assembly of the drill guide, stylus and body in which the drill guide 54 is slidably mounted on member 6 and with shaft 30 of the stylus received in the channel of member 6 of the size guide body.

Figure 7:
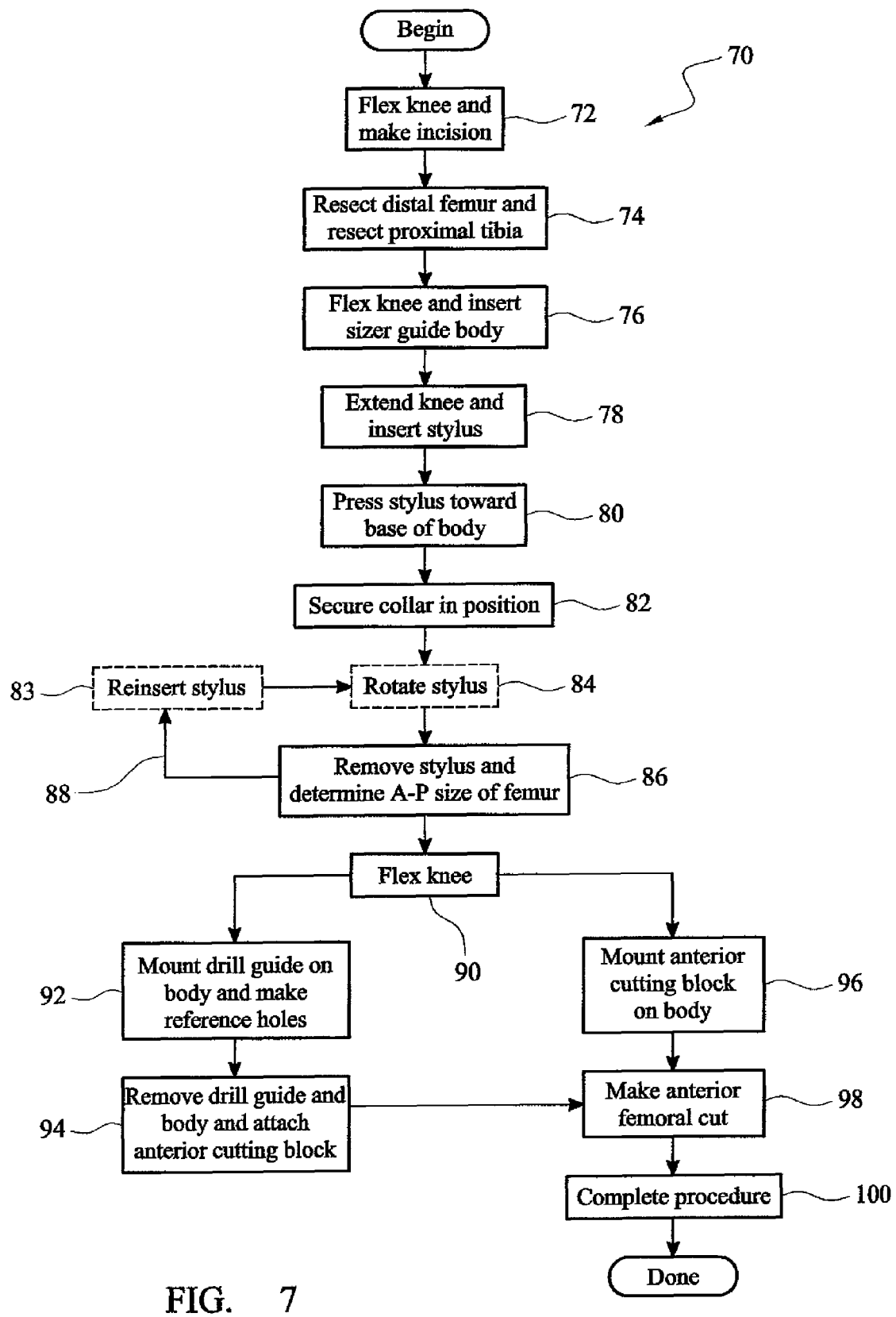
FIG. 7 shows a flow chart illustrating a minimally invasive surgical method aspect of the present invention.

A method 70 of using the femoral size guide of the present invention is shown in FIG. 7. The knee joint is placed in flexion and an incision is made in the knee 72. The distal femur is resected and then the proximal tibia is resected 74. Resection of the femur and tibia provides an extension gap of about 20 mm. The size guide body 2 of the present invention is inserted between the distal femur and the proximal tibia with the knee in flexion 76. The base 4 of the size guide body 2 contacts the posterior condyles. The first 20 and second 22 feet of the base 4 of the size guide body contact the posterior condyles. The spikes 24 of the base 4 contact the distal femur and secure the size guide body in position. The knee joint is placed in extension 78 and the tubular member 6 of the size guide body is present between the proximal tibia and the distal femur. The tubular member 6 has a cross-sectional dimension of less than about 20 mm.

The first end 32 of the elongated shaft 30 of the stylus 28 is inserted 78 into the channel of the tubular member 6 of the size guide body 2. The elongated shaft 30 of the stylus 28 is further inserted 80 into the channel of the tubular member 6 until the tip of the stylus contacts with the distal femur. The collar 50 slides from the second end 34 of the elongated shaft 30 towards the first end 32 of the elongated shaft 30 until the collar 50 contacts the second end 10 of the tubular member 6 of the size guide body 2. In an alternate embodiment, the collar has a friction fit around shaft 30 and the collar is initially positioned toward the lower end of shaft 30 so that as shaft 30 is inserted into the channel 6 in the base, the end 10 of the base pushes collar 50 up the shaft 30 as the shaft is inserted until the tip of the stylus contacts the femur.

The locking member 52 is then used to secure collar 50 in position 82 against the elongated shaft 30 of the stylus 28. The stylus 28 is then removed 86 from the size guide body 2. The anterior-posterior dimension of the distal femur is then determined by reading the position of the collar 50 on the scale of markings 38 on by the stylus part 28. The position of the arm 36 relative to the channel 42 provided in the second end 34 of the elongated shaft 30 of the stylus 28 can also be adjusted.

The position of the arm 36 is moved in channel 42 based on the scale of markings provided by the arm 36 to correspond to the dimensions of the implant required for the determined anterior-posterior size of the implant. The first portion 44 of the arm 36 is slidably moved within the channel 42 provided by the second end 34 of the elongated shaft 30 of the stylus. The first portion 44 of the arm 36 is adjusted so that the marking present at either end of the channel 42 corresponds to the anterior-posterior size of the required implant.

The stylus 28 with the collar 50 secure in position along the elongated shaft 30 is re-inserted into the size guide body 2 at step 83. Once in position, the surgeon uses the handle 48 to rotate the arm 36 of the stylus about the longitudinal axis of the elongated member 30 at step 84. The elongated member 30 rotates within the tubular member 6 of the size guide body and traces the tip over the surface of the femur. The surgeon is able to assess whether the dimensions of the implant as determined by the position of the collar 50 on the elongated shaft 30 of the stylus 28 is correct for the patient's femur. The surgeon may carry out an iterative procedure by altering one or more of the position of the arm 36 within channel 42 or the position of the collar 50 on the elongated shaft 30 as illustrated schematically by loop 88.

Rotating the stylus to check whether the size of implant indicated by the collar 50 is appropriate for the patients femur is optional as indicated by boxes 84 and 83 being illustrated in broken lines and may not need to be carried out.

Once the surgeon is satisfied that the readings have provided the correct size of implant to be used for the patient the stylus 28 is removed from the size guide body 2.

The knee is then placed in flexion at step 90. Two alternative approaches may the be used. In a first approach the drill guide 54 is then inserted over the tubular member 6 of the size guide body 2. The drill guide 54 is placed at the appropriate height on member 6 as indicated by pointer 68 on scale 26 on the tubular member 6 of the size guide body 2 for the selected size of implant and locked in position using screw fastener 66. Reference holes are then made via apertures 62 and 66. Either the upper or the lower hole in each aperture can be used to provide some further control or fine tuning over the anterior-posterior positioning of the implant, or a small amount of rotation by using an upper hole for one side and a lower hole for the other side. The drill guide 54 and the size guide body 2 are removed at step 94 and a suitable anterior cutting block is attached to the reference holes in the femur.

In a second approach a suitable anterior cutting block is inserted over the tubular member 6 of the size guide body 2 at step 96. The anterior cutting block is placed in position according to the scale of markings 26 on the tubular member 6 of the size guide body 2 for the selected size of implant and the anterior cutting block is secured in place. Then the anterior femoral cut is made at step 98 using the cutting block. The remaining steps of the surgical procedure are then carried out at step 100 in order to complete the minimally invasive knee arthroplasty.

The invention claimed is:

1. An instrument for use in determining an anterior-posterior dimension of a femur during a minimally invasive surgical procedure comprising:
   a body comprising:
      a base, and a member extending upwardly from the base;
   a stylus comprising:
      a stylus support, the stylus support engaging with the member to allow relative sliding movement between the stylus and base, the stylus support having a scale indicating a size of an implant, and
      a stylus member mounted on the stylus support; and
   a collar slideably mounted on the stylus support and moveable relative to the scale.

2. The instrument of claim 1, wherein the stylus support and the upwardly extending member part of the body provide between them a telescoping sliding arrangement, wherein one of the stylus support and the upwardly extending member part of the body provides a shaft and the other of the stylus support and the upwardly extending member part of the body provides a socket in which the shaft can slide, and wherein the collar is slideably mounted on the shaft.

3. The instrument of claim 2, wherein the shaft is provided by the stylus support and the socket is provided by the upwardly extending member art of the body.

4. The instrument of claim 1, further comprising a locking member for fixing the position of the collar relative to the scale.

5. The instrument of claim 1, wherein the scale comprises markings to indicate a position of the stylus support relative to the upwardly extending member.

6. The instrument of claim 1, wherein the stylus member can translate and/or pivot relative to the stylus support.

7. The instrument of claim 1, wherein the stylus member comprises a first portion and a second portion, the first portion extending from the stylus support in a direction transverse to a longitudinal axis of the stylus support and the second portion extending downwardly toward the base.

8. The instrument of claim 1, wherein the stylus member comprises a first portion and a second portion, the first portion providing a handle which extends from the stylus support and the second portion extending along an arc and terminating in a stylus tip.

9. The instrument of claim 1, wherein the body comprises at least one foot that extends from the base and faces a posterior condyle surface of the femur when the base contacts the distal end face of the femur.

10. The instrument of claim 9, wherein the body comprises two spaced limbs that extend from the base.

11. The instrument of claim 1, wherein the base of the body has at least one spike extending from the base for contacting the distal end face of the femur.

12. The instrument of claim 1, wherein the thickness of the base of the body is less than about 17 mm.

13. The instrument of claim 1, wherein the greatest thickness of the member of the body is less than about 17 mm.

14. The instrument of claim 1, further comprising at least a drill guide or an anterior cutting block that can slidingly engage with the member of the body.

15. A method for determining the anterior-posterior dimension of a distal femur during surgical procedure using the instrument of claim 1, comprising the steps of:
while the knee joint is in flexion, inserting the body of the instrument between a resected distal femur and a resected proximal tibia so that the base of the body contacts the posterior condyles of the distal femur;
slidingly engaging the stylus with the body;
while the knee joint is in extension, sliding the stylus relative to the body until the stylus member contacts a portion of the distal femur; and
determining the anterior-posterior size of the distal femur from the position of the collar relative to the scale, the collar having been caused to move relative to the stylus by the relative sliding movement of the stylus and the body.

16. A method as claimed in claim 15, further comprising at least one of the following steps:
adjusting the length of the stylus member;
re-engaging the stylus with the body; or
rotating the stylus member relative to the body.

17. A method for making an anterior femoral cut at the distal end of a femur, comprising:
determining the anterior-posterior dimension of the distal femur using the method as claimed in claim 15;
flexing the knee joint and slidingly engaging a drill guide with the body to a position required by an implant size as indicated by the position of the collar relative to the scale;
drilling reference holes in the femur using the drill guide;
removing the drill guide and the body;
securing an anterior cutting block to the reference holes in the femur; and
making the anterior femoral cut using the anterior cutting block.

18. A method for making an anterior femoral cut at the distal end of a femur, comprising:
determining the anterior-posterior dimension of the distal femur using the method as claimed in claim 15;
flexing the knee joint and slidingly engaging an anterior cutting block with the body to a position required by an implant size as indicated by the position of the collar relative to the scale; and
making the anterior femoral cut using the anterior cutting block.

* * * * *